(12) United States Patent
Kodaira

(10) Patent No.: US 9,414,793 B2
(45) Date of Patent: Aug. 16, 2016

(54) X-RAY CT SYSTEM
(71) Applicant: Toshiba Medical Systems Corporation, Otawara-shi (JP)
(72) Inventor: Yasuo Kodaira, Utsunomiya (JP)
(73) Assignee: Toshiba Medical Systems Corporation, Otawara-shi (JP)
( * ) Notice: Subject to any disclaimer, the term of this patent is extended or adjusted under 35 U.S.C. 154(b) by 37 days.
(21) Appl. No.: 14/235,687
(22) PCT Filed: Feb. 20, 2013
(86) PCT No.: PCT/JP2013/054235
 § 371 (c)(1),
 (2) Date: Jan. 28, 2014
(87) PCT Pub. No.: WO2013/125602
 PCT Pub. Date: Aug. 29, 2013
(65) Prior Publication Data
 US 2014/0169532 A1    Jun. 19, 2014
(30) Foreign Application Priority Data

Feb. 22, 2012  (JP) ................................ 2012-036172

(51) Int. Cl.
 *H05G 1/02*      (2006.01)
 *G10K 11/00*     (2006.01)
          (Continued)
(52) U.S. Cl.
 CPC ... *A61B 6/44* (2013.01); *E04B 1/82* (2013.01); *E04B 1/84* (2013.01); *E04F 13/075* (2013.01);
          (Continued)
(58) Field of Classification Search
 CPC .................. A61N 2005/10; A61N 2005/1092; A61B 6/00; A61B 6/10; A61B 6/102; A61B 6/44; A61B 6/4423; A61B 6/4429; A61B 6/4435; G10K 11/00; H05G 1/00; H05G 1/02; H05G 1/04; E04B 1/62; E04B 1/74; E04B 1/82; E04B 1/8209; E04B 1/84; E04B 1/8409; E04B 2001/742; E04B 2001/748; E04B 2001/8476; E04F 13/07; E04F 13/072; E04F 13/075; E04F 13/076; E04F 13/077; E04F 13/08; E04F 13/0801; E04F 13/0866; E04F 13/0896; E04F 13/0898; E04F 13/18; E04F 2290/00; E04F 2290/04; E04F 2290/041; E04F 2290/042; E04F 2290/043
 See application file for complete search history.

(56) References Cited

U.S. PATENT DOCUMENTS 3,322,233 A * 5/1967 McCluer ................... E04B 1/84
                                                    181/290
4,881,251 A   11/1989 Nambu et al.
          (Continued)

FOREIGN PATENT DOCUMENTS

CN     101061955 A    10/2007
CN     101761732 A    6/2010
          (Continued)

OTHER PUBLICATIONS

International Search Report issued May 14, 2013, in PCT/JP13/054235 filed Feb. 20, 2013.
          (Continued)

*Primary Examiner* — Anastasia Midkiff
(74) *Attorney, Agent, or Firm* — Oblon, McClelland, Maier & Neustadt, L.L.P.

(57) ABSTRACT

An X-ray CT system as the embodiment comprises an annular rotating body configured to accommodate an X-ray tube, the rotating body having a central opening, into which a bed can be inserted in the center thereof, a cover shaped in a tubular form and having a tubular case part, which, when fitted in the opening, shields the annular rotating body from a central side of the opening, the cover being provided with an X-ray transmission opening at the tubular case part, through which, X-rays from the X-ray tube are allowed to transmit, and two sheet-like soundproof members configured to sandwich a soundproof layer, the soundproof members being disposed to to close the X-ray transmission opening. According to the X-ray CT system, it is possible to reduce sufficiently the noise leaking from inside the cover.

12 Claims, 7 Drawing Sheets

(51) Int. Cl.
*E04B 1/82* (2006.01)
*E04B 1/84* (2006.01)
*E04F 13/075* (2006.01)
*E04F 13/077* (2006.01)
*A61B 6/00* (2006.01)
*E04F 13/08* (2006.01)
*A61B 6/03* (2006.01)
*A61B 6/08* (2006.01)

(52) U.S. Cl.
CPC ........... *E04F 13/077* (2013.01); *E04F 13/0866* (2013.01); *G10K 11/00* (2013.01); *H05G 1/02* (2013.01); *A61B 6/035* (2013.01); *A61B 6/08* (2013.01); *A61B 6/4488* (2013.01); *A61B 6/56* (2013.01); *E04B 1/8209* (2013.01); *E04B 1/8409* (2013.01); *E04B 2001/8476* (2013.01); *E04F 2290/041* (2013.01)

(56) References Cited

U.S. PATENT DOCUMENTS

2008/0165915 A1* 7/2008 Battle ................. A61B 6/00 378/4
2009/0141853 A1* 6/2009 Crews ................. A61B 6/032 378/4
2012/0229138 A1* 9/2012 Saha ................. G01R 33/3854 324/318
2013/0129104 A1* 5/2013 Joshi ................. A61B 6/032 381/71.3
2013/0161126 A1* 6/2013 Wilson ................. E01F 8/0088 181/290

FOREIGN PATENT DOCUMENTS

| JP | 63-38438 | 2/1988 |
| JP | 2-124139 | 5/1990 |
| JP | 3-162831 | 7/1991 |
| JP | 5-124308 | 5/1993 |
| JP | 8-257008 | 10/1996 |
| JP | 11-64599 | 3/1999 |
| JP | 2010-284302 | 12/2010 |

OTHER PUBLICATIONS

Combined Chinese Office Action and Search Report issued Jul. 3, 2015 in Patent Application No. 201380003062.1 (with English translation of categories of cited documents).

* cited by examiner

X-RAY CT SYSTEM

TECHNICAL FIELD

Embodiments of the present invention relate to X-ray CT systems.

BACKGROUND ART

A conventional X-ray CT system detects X-rays emitted from an X-ray tube and transmitted through the subject, and reconstruct images based on detection results to obtain an X-ray tomographic image. In the X-ray CT system, the X-ray tube is provided inside an annular rotating body, whose center is a through-opening, into which a bed with the subject can be inserted. The annular rotating body is circumferentially shielded with a cover, which comprises a tubular case part for shielding the annular rotating body, the cover extending from the central side of the opening. Moreover, the tubular case part is provided with an X-ray transmission opening, where X-rays from the X-ray tube pass through.

The X-ray transmission opening is, however, closed with a sheet member for the purpose of ensuring safety. The sheet member prevents the subject from coming into contact with the annular rotating body, and it also protects the interior of the annular rotating body against penetration of blood or contrast agents. Furthermore, the sheet member prevents noise from coming out of the inside of the cover. The noise inside the cover includes a wind noise caused by the rotation of the annular rotating body and the sound of the motor driving it.

The sheet member comprises a thin film-like material having a high transmittance for X-rays and a laser beam that is used for marking the subject. This can suppress deterioration in the quality of images acquired by radiography.

As another type of medical diagnostic apparatus, for example, an MRI system, is provided with a sound absorption material that is applied as a lining to the internal surface of the cover. The silencing effect of the material reduces the noise leaking out of the machine see Japanese Laid-Open Patent Publication No. H8-257008)

SUMMARY OF THE INVENTION

Problems to be Solved by the Invention

However, the simple closing of the X-ray transmission opening with the sheet member or with the sound absorption material, which is mentioned in Patent reference 1, does not sufficiently reduce the noise that leaks out from inside the cover. It has been a problem.

The object of this embodiment is to solve the above-mentioned problem and to provide an X-ray CT system that is capable of sufficiently reducing the noise leaking from inside the cover.

Means for Solving the Problems

To solve the above-mentioned problem, an X-ray CT system as the embodiment comprises an annular rotating body configured to accommodate an X-ray tube, the rotating body having a central opening, into which a bed can be inserted in the center thereof, a cover having a tubular case part, shaped in a tubuar form, which is fitted in the opening to shield the annular rotating body from a central side of the opening, the cover being provided with an X-ray transmission opening at the tubular case part, through which, X-rays from the X-ray tube are allowed to transmit, and two sheet-like soundproof members configured to sandwich a soundproof layer, the soundproof members being disposed to close the X-ray transmission opening.

PREFERRED EMBODIMENTS OF THE INVENTION

Figure 1:
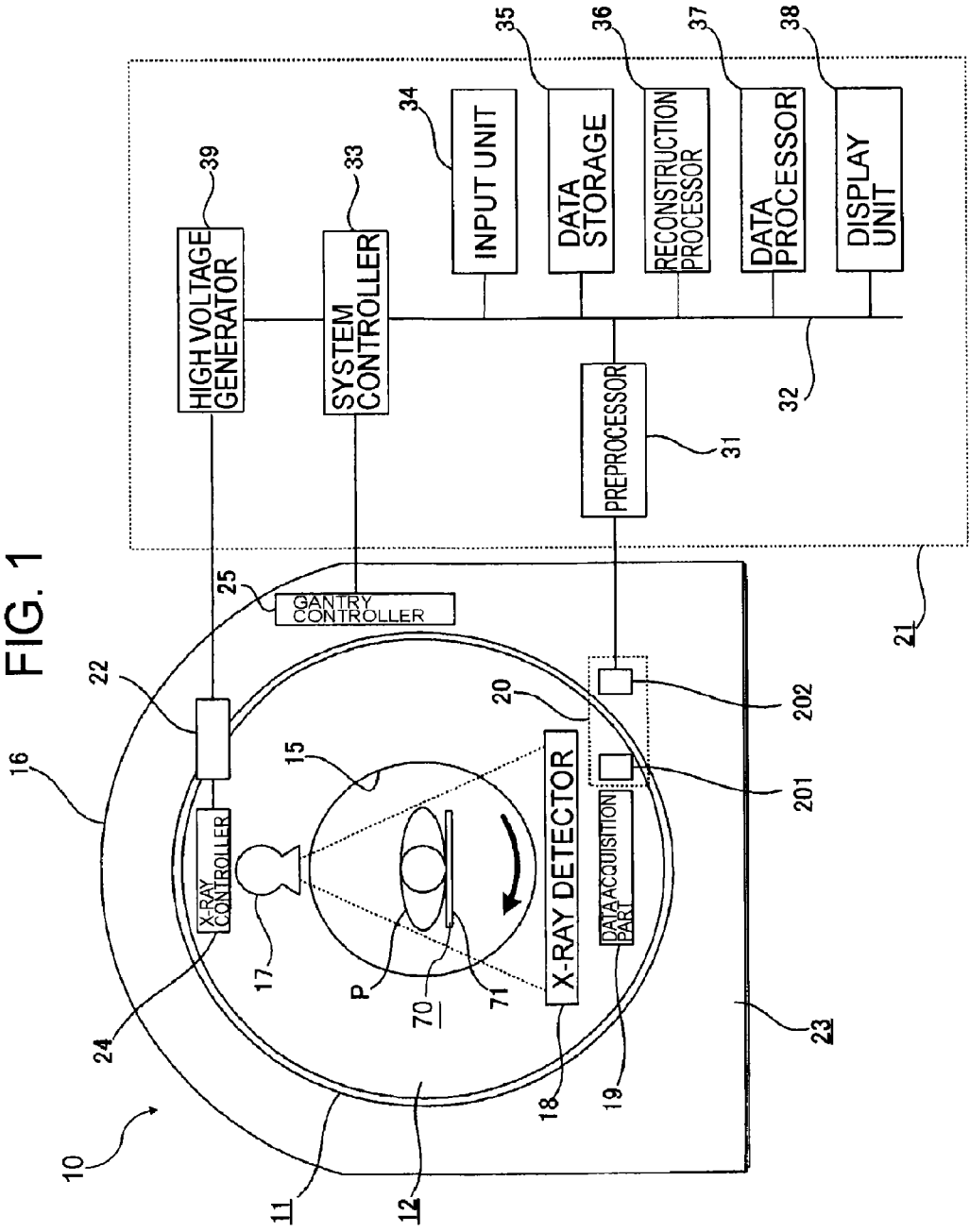
FIG. 1 is a block diagram showing an X-ray CT system as an embodiment.

An embodiment of this type of X-ray CT system is described with reference to FIG. 1. FIG. 1 is a block diagram showing the X-ray CT system.

The X-ray CT system shown in FIG. 1 is an example of X-ray CT system used for medical diagnosis. The X-ray CT system 10 comprises a gantry 11, an annular rotating body 12, a rotary mechanism 14, a cover 16, a cooler 40, and a duct 50.

The annular rotating body 12 and the rotary mechanism 14 are disposed at the inner side of the gantry 11, and the annular rotating body 12 is driven and rotated by the rotary mechanism 14.

The annular rotating body 12 is internally provided with an X-ray tube 17 and an X-ray detector 18. Provided in the center of the gantry 11 and the annular rotating body 12 is an opening 15, into which a subject P placed on the top plate 71 of a bed 70 is inserted from the front of the gantry.

The cover 16 is formed so as to shield the gantry 11 and the annular rotating body 12. By the way, the details of the cover 16 are described later.

The X-ray tube 17 and the X-ray detector 18 are disposed facing each other, with the opening 15 being positioned in the middle. X-rays from the X-ray tube 17 are directed to irradiate the subject P, and X-rays that have transmitted through the subject P are detected by the X-ray detector 18 to be converted into electrical signals. The electrical signals are amplified by the data acquisition system (DAS) 19 and are converted into digital data. By the way, the mechanism provided for cooling the X-ray tube 17 (cooling mechanism) will be detailed later.

The X-ray detector 18 comprises, for example, an array of detector elements like a scintillator array or a photodiode array, and the elements are arranged along an arc whose center coincides with the focal point of the X-ray tube 17. Furthermore, the digital data (projection data) from the DAS 19 are transmitted through a data transmitter 20 to the console 21.

The data transmitter 20 is configured to transmit projection data from the annular rotating body 12 to the console 21 in a contact-less manner. The data transmitter 20 comprises a transmitter 201, which is provided on the annular rotating body 12, and a receiver 202, which is provided on the stationary part of the gantry 11. Data received by the receiver 202 is supplied to the console 21. The transmitter 201 is attached on the annular rotating body, while the receiver 202 is attached on a annular stationary body.

In addition, the annular rotating body 12 includes a slip ring 22 and an X-ray controller 24. The stationary part 23 is provided with a gantry controller 25.

The console 21 constitutes a computer system. Projection data transmitted from the data transmitter 20 are supplied to a preprocessor 31. The preprocessor 31 executes preprocessing such as data correction on the projection data and outputs the preprocessed data onto bus lines 32.

Connected to the bus lines 32 are a system controller 33, an input unit 34, a data storage 35, a reconstruction processor 36, a data processor 37, a display unit 38, etc. The high voltage generator 39 is connected to the system controller 33.

The system controller 33 functions as host controller, and it controls the actions of each part of the console 21 and controls the gantry controller 25 and the high voltage generator 39. The data storage 35 stores data of tomographic images, and the reconstruction processor 36 reconstructs 3D image data from projection data. The data processor 37 processes image data stored in the data storage 35 or image data that have been reconstructed. The display unit 38 displays images that have been obtained by image-data processing.

The input unit 34 comprises a key-board, a mouse, etc. and is operated by the user (physician, operator, and others) for setting up various parameters for data processing. In addition, it is used for inputting variety of information regarding the state of the subject P or the procedure for the examination.

The high voltage generator 39 controls the X-ray controller 24 through the slip ring 22 and supplies electrical power to the X-ray tube 17, i.e., the electrical power (tube voltage and tube current) necessary to radiate X-ray. The X-ray tube 17 generates an X-ray beam that spreads toward two directions, i.e., the slicing direction, in parallel with the axial direction of the subject P, and the channeling direction perpendicular to the slicing direction. The flare angle of X-ray beams in the slicing direction may be sometimes referred to as a "cone angle", while the flare angle in the channeling direction may be referred to as a "fan angle".

The system is provided with a laser projector (not shown), for the purpose of marking (the body surface). The marking is performed by irradiating colored laser beams for the body surface of the subject P from the side and above. As the colored laser beams, for example, red laser and green laser are desirable because they are easily recognized (visible) as marking.

[Cover]

Figure 2:
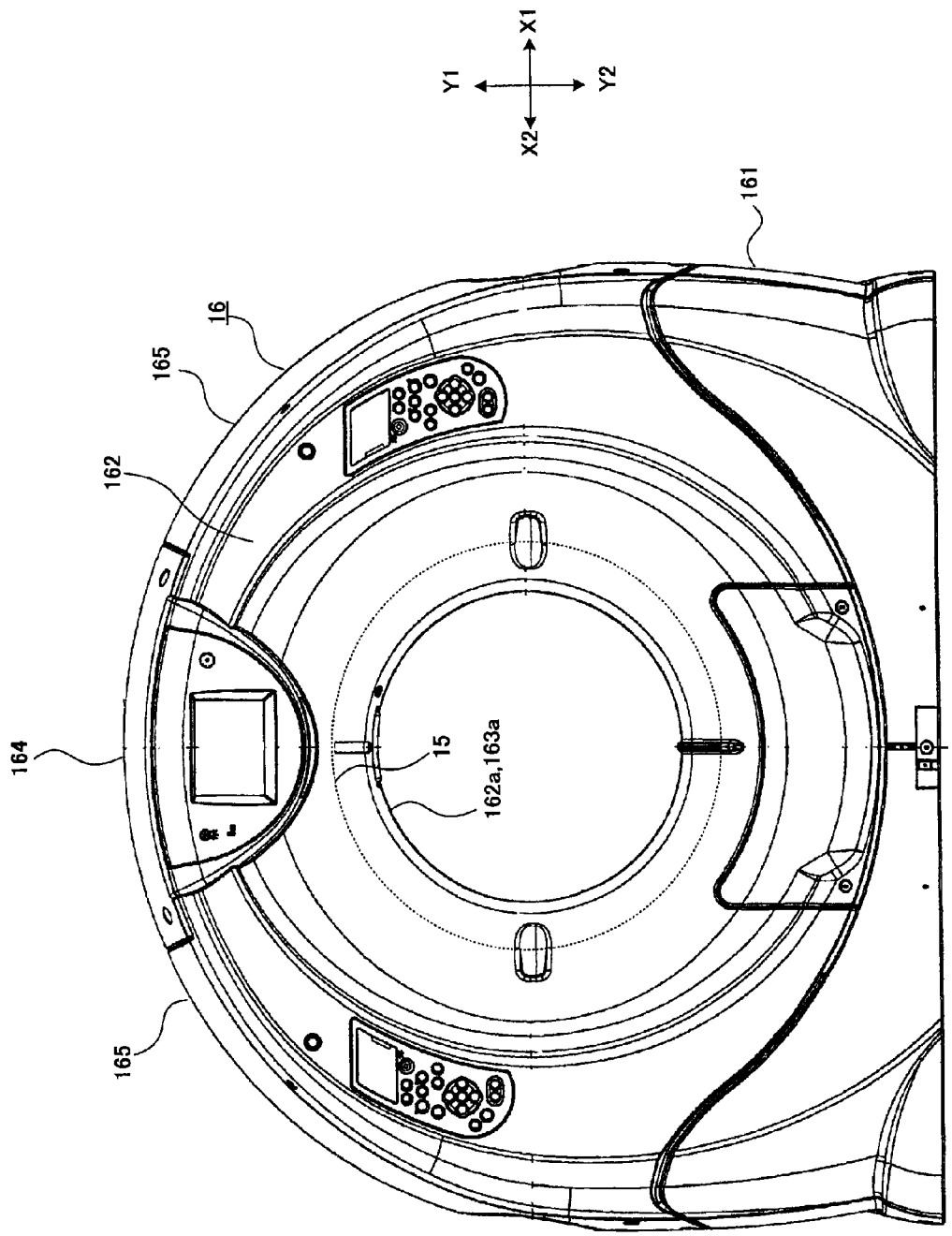
FIG. 2 is a front view of the X-ray CT system.

The above description has been about the basic configuration of the X-ray CT system. Now, the details of the cover 16 are described with reference to FIG. 2 and FIG. 3. FIG. 2 is a front view of the X-ray CT system while FIG. 3 is a perspective view of the X-ray CT system looked at from a diagonal rear.

Here, the parts of the gantry 11 that correspond, respectively, to the front part, the rear part, both the lateral parts, the upper part, and the lower part of the annular rotating body 12 are sometimes called to, respectively, as front part, rear part, lateral parts, ceiling part, and bottom part. In addition, the right and left directions (both lateral directions), the up and down direction (height direction), and the axial direction (front and rear direction) are sometimes called to, respectively, as X-axis direction, Y-axis direction, and Z-axis direction. The rear part of the gantry 11 may be referred to as frame 13.

Figure 3:
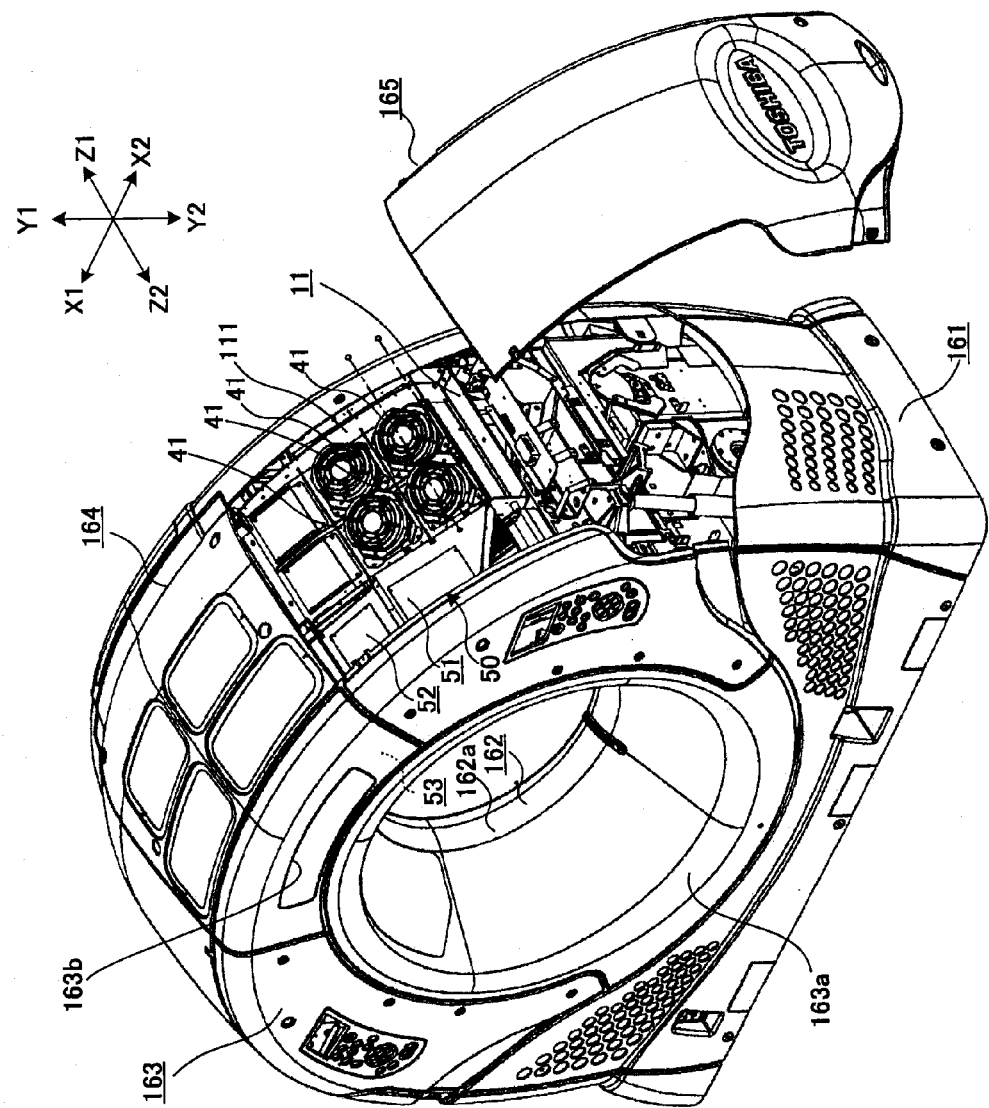
FIG. 3 is a perspective view of the X-ray CT system looked at from a diagonal rear.

Furthermore, in FIGS. 2 and 3, the frontward and rearward directions of the annular rotating body 12 are indicated, respectively, with arrows Z1 and Z2; the rightward and leftward directions of the annular rotating body 12 are indicated, respectively, with arrows X1 and X2; and the upward and downward directions of the to annular rotating body 12 are indicated, respectively, with arrows Y1 and Y2.

As shown in FIG. 2 and FIG. 3, the cover 16 comprises a bottom cover 161, which shields the bottom of the gantry 11, a front cover 162, which shields the front part of the gantry 11, a rear cover 163, which shields the rear part of the gantry 11, a ceiling cover 164, which shields the ceiling part of the gantry 11, and lateral covers 165, which shield the lateral parts of the gantry 11.

The front cover 162 includes a tubular opening front part 162a. The tubular opening front part 162a, which is shaped in a tubular form, is fitted into the opening (central opening) 15 from the front, so as to shield approximately the front half of the opening 15 from the Z-axis direction (axial direction).

The rear cover 163 includes a tubular opening rear part 163a. The tubular opening rear part 163a, which is shaped in a tubular form, is fitted into the opening 15 from the rear, so as to shield approximately the rear half of the opening 15 from the Z-axis direction. The tubular case part is configured with the tubular opening front part 162a and the tubular opening rear part 163a.

The rear cover 163 is provided with a vent 163b at the upper part to release heat from a radiator out of the cover 16. The radiator will be described later. The vent 163b is located at the position that corresponds to the clock position of twelve o'clock in FIGS. 2 and 3. Since the heat from the radiator rises inside the cover 16, the heat is efficiently released through the vent 163b, which is located at the upper part of the rear cover 163. The noise coming through the vent 163b from inside the cover 16 to the front side of the X-ray CT system is much reduced compared to other configurations in which the vent 163b is provided at the front cover 162 or at the front part of the bottom cover 161.

It is preferable that the vent 163b is arranged at the upper part of the cover 16, for the purpose of efficiently releasing heat from the radiator. The vent 163b may be also provided, for example, through the ceiling cover 164.

The rear cover 163 shields part of a duct 50, which will be described later. In addition, the lateral covers 165 shield other part of the duct 50 and a fan 41, which will be also described later. The other part of the duct 50 and the fan 41 may be shielded by another part of the cover 16, for example, the ceiling cover 164.

[Cooler and Duct]

The cooler has a fan 41. The fan 41 is disposed in the vicinity of the radiator 26 and ejects heat from the radiator 26 into the duct 50. The duct 50 is disposed between the gantry 11 and the cover 16, and it receives the air from the fan 41 and leads the air to the vent 163b. The noise coming from inside the cover includes a wind noise caused by the rotating fan 41 and the sound of the motor driving it.

[Soundproof Construction]

Described below is a soundproof construction that reduces the noise coming from inside the cover 16.

(Soundproof Construction as Contrastive Example)

Figure 4:
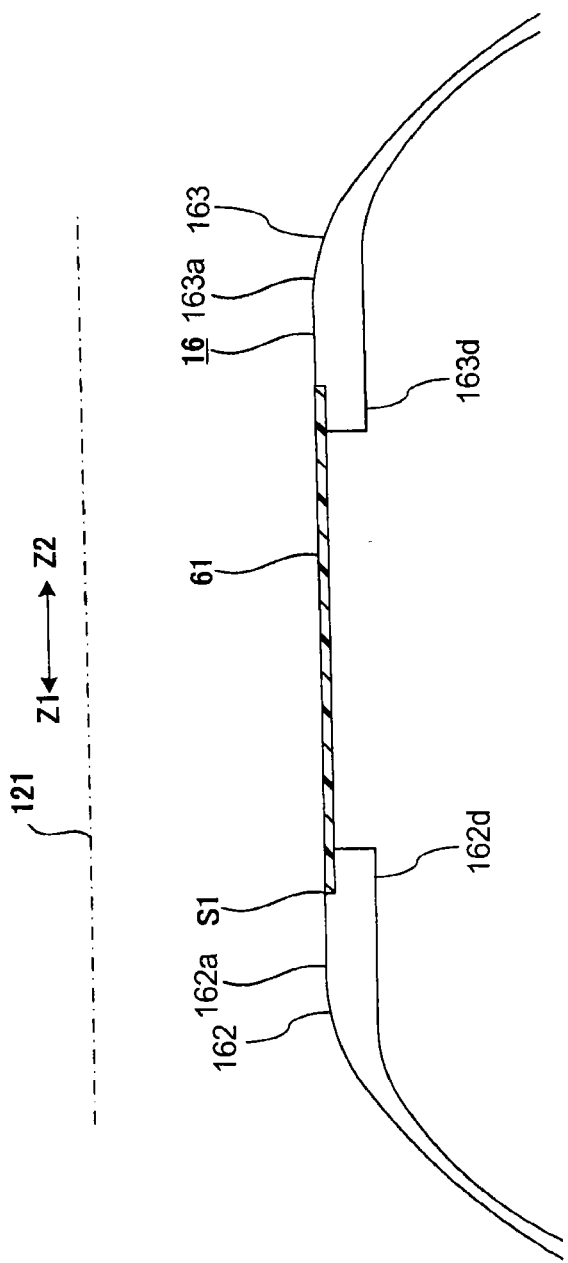
FIG. 4 is a sectional view of a soundproof construction that does not include a soundproof layer, presented as a contrastive example.

At first, a contrastive example of a soundproof construction is described with reference to FIG. 4. FIG. 4 is a sectional view of a soundproof construction configured to include one soundproof member, depicted with the opening 15 along the axial axis (Z-axis).

As shown in FIG. 4, the X-ray transmission opening S1, which lets X-rays pass through, is positioned between the rear end 162d of the tubular opening front part 162a of the front cover 162 and the front end 163d of the tubular opening rear part 163a of the rear cover 163. The circumferential width of the X-ray transmission opening S1 corresponds to the fan angle of X-ray beams. The width in the Z-axis direction of the X-ray transmission opening S1 corresponds to the cone angle of X-ray beams.

As shown in FIG. 4, the X-ray transmission opening S1 is closed with a sheet-like soundproof member 61. Therefore, it is possible to ensure safety so that the subject P never comes into contact with the annular rotating body 12. It is also possible to protect intrusion of the interior of the annular rotating body 12 against accidental penetration of blood or contrast agents. Furthermore, it prevents noise leaking out through the cover 16.

(Relation between Thickness of Soundproof Member and Sound Transmission Loss)

Figure 5:
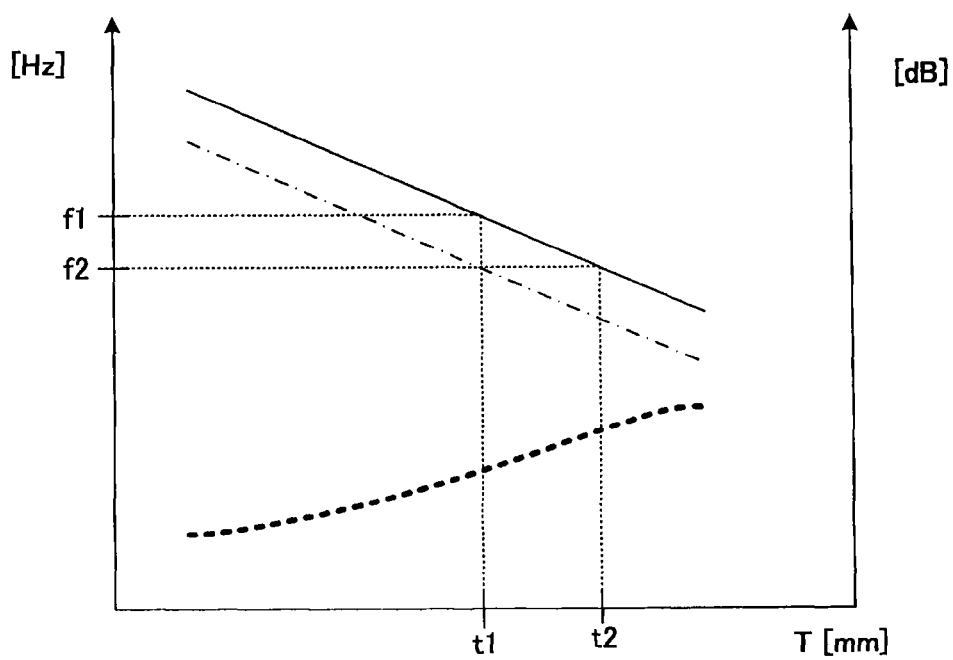
FIG. 5 is a graph showing relations between the thickness of a soundproof member and the value of sound transmission loss.

Here, the relation between the thickness of the soundproof member 61 and sound transmission loss is explained with reference to FIG. 5. FIG. 5 is a graph showing the relation between the thickness of the soundproof member and the value of sound transmission loss. Here, the value of sound transmission loss is the amount that is obtained by multiplying the logarithm of the reciprocal of acoustic transmission coefficient by 10, and it is expressed in decibels [dB]. The acoustic transmission coefficient is the ratio of transmitted sound intensity to incident sound intensity.

FIG. 5 is a graph whose horizontal axis represents the thickness [mm] of the soundproof member and whose vertical axis represents the value of sound transmission loss, along with frequencies [Hz] of coincidence effect. Here, the term "coincidence effect" means a phenomenon that the value of sound transmission loss decreases at a particular frequency.

In FIG. 5, the solid line indicates the frequency at which a coincidence effect occurs for the thickness T of the soundproof member 61 without a soundproof layer 62; the dash-dot line indicates the frequency at which a coincidence effect occurs for the thickness T of the soundproof member 61 with a soundproof layer 62; and the dashed line indicates the value of sound transmission loss for the thickness T of the soundproof member 61.

The value of sound transmission loss rises as the thickness T of the soundproof member 61 increases, resulting in an improvement in acoustic insulation. In addition, the frequency at which a coincidence effect occurs moves to the side of lower tone as the thickness T of the soundproof member 61 increases. The frequency when the thickness T is "t1" is indicated by "f1" in FIG. 5. However, depending on the frequency characteristics of noises, the increased thickness T does not always lead to an improvement in acoustic insulation. For example, if the noise includes the frequency f1 at which a coincidence effect takes place, then the value of sound transmission loss drops and the acoustic insulation drops. For this reason, it is necessary to make the thickness T of the soundproof member 61 thinner than an upper limit t1 (T <t1).

The above description has been about a soundproof construction that is configured with one soundproof member 61. It should be understood here that there is a difficulty in improving the sound insulation property of the system by applying only one soundproof member 61.

(Soundproof Construction with Soundproof Layer)

Figure 6:
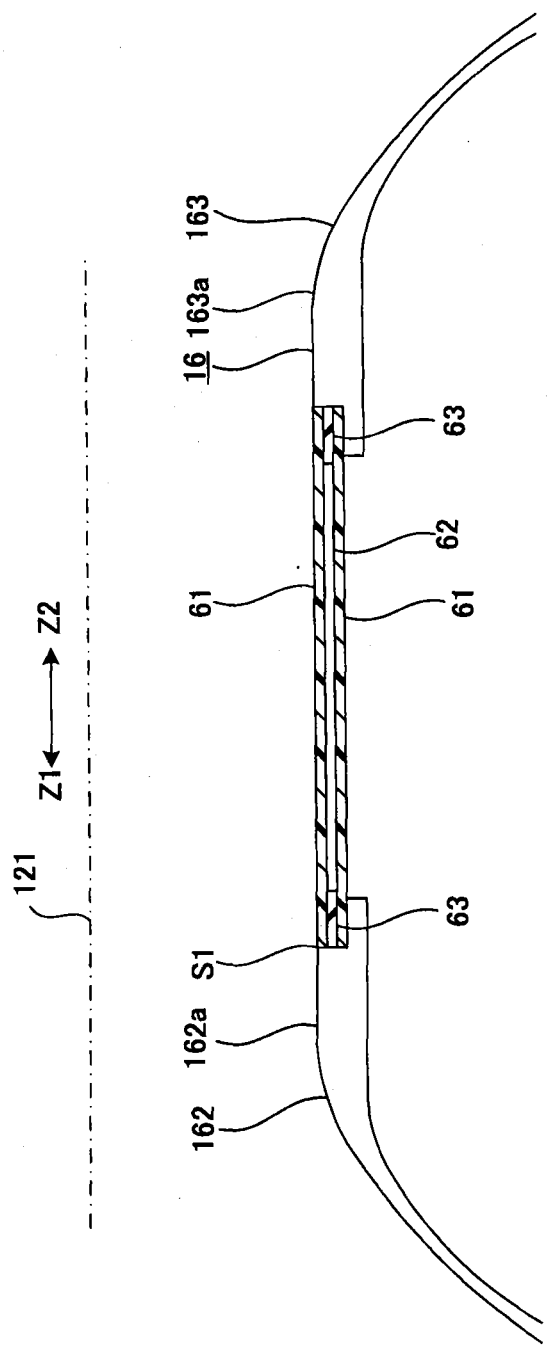
FIG. 6 is a sectional view of a soundproof construction that includes a soundproof layer.

Now, the soundproof construction of this embodiment is described with reference to FIG. 6 and FIG. 7. FIG. 6 is a sectional view of the soundproof construction, which includes a soundproof layer, depicted with the central opening 15 along the axial axis (Z-axis).

As shown in FIG. 6, the soundproof construction of the present embodiment comprises two soundproof members 61 and a soundproof layer 62 for improving the sound insulation property. The soundproof layer 62 is an air layer. Note that the soundproof construction may comprise two or more sets of the combination of two soundproof members 61 and one soundproof layer 62. Furthermore, the soundproof layer 62 may include an acoustic absorption member and/or an acoustic reflection member.

Figure 7:
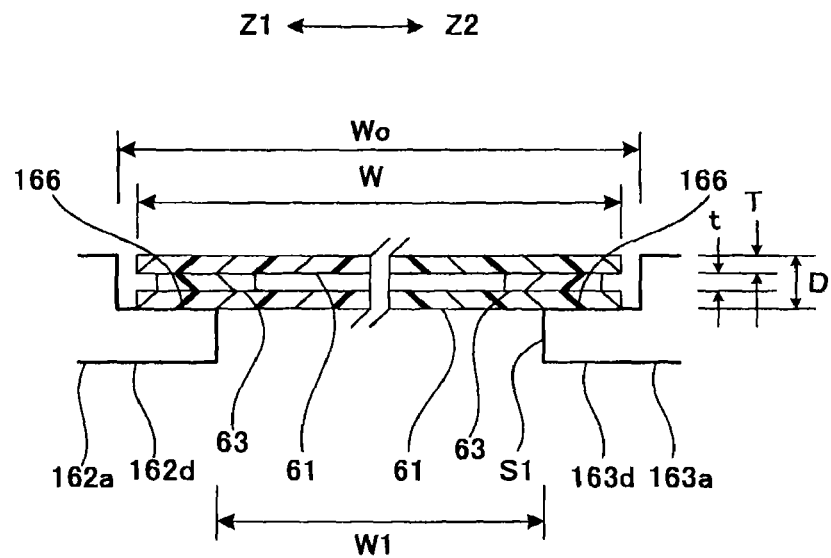
FIG. 7 is an enlarged sectional view partially showing the soundproof member.

FIG. 7 is a partially enlarged sectional view of the soundproof members. As shown in FIG. 6 and FIG. 7, as the soundproof construction, two soundproof members 61 are disposed so as to sandwich an air layer as a soundproof layer 62. These two soundproof members 61 are disposed to bridge over the X-ray transmission opening S1. Although FIG. 6 and FIG. 7 show the two soundproof members 61 being disposed in parallel, the configuration is not restricted to this. The two soundproof members 61 may be disposed with a predetermined angle between them.

(Soundproof Member)

The soundproof member 61 comprises a thin film-like material that has a high sound transmission loss and a high transmittance for X-rays and laser beams used for marking. It is possible to limit deterioration to the quality of images acquired by radiography.

The types of materials for the soundproof member 61 include acoustic absorption material, which has a property of converting part of sound energy into heat energy and reducing sound reflection, and acoustic reflection material, which has a property of reflecting and refracting incident sound.

The examples of acoustic absorption material include a fibrous member and a sponge-like member that has a lot of small pores. It is preferable that a porous material such as glass-wool or urethane be used as a leading example of acoustic absorption material.

For example, the acoustic reflection member may be configured by enclosing, between two soundproof members, a gas like helium, which has a property of faster acoustic transmission than air.

In this embodiment, for example, polyethylene terephthalate (PET) is used for the soundproof member 61. As a PET, it is preferable to choose Mylar (registered trademark).

The resin materials used for the soundproof member 61 are, however, not limited to PET, and they can be any materials that have a high transmittance for X-rays and laser beams and a low resistance to deterioration of X-ray.

It is preferable that the thickness of the soundproof member 61 be 0.5 mm -1.0 mm. The reason why the lower limit is set at 0.5 mm is that even if the subject P should come into contact with the soundproof member 61, the thickness equal to or more than 0.5 mm can secure the safety of the subject. Furthermore, the reason why the upper limit is set at 1.0 mm is that the thickness equal to or less than 1.0 mm can ensure a good transmittance of X-rays and laser beams for the soundproof member. Conversely, if the thickness is more than 1.0 mm, then the soundproof member absorbs X-rays and laser beams. The X-ray absorption by the soundproof member causes to deteriorate the quality of resultant images, and the laser beam absorption causes to lost the easy recognition of the above-mentioned laser marking.

Now, more details are given of the soundproof member 61 that is made of the above-mentioned material and to the above-mentioned thickness.

The soundproof member 61 may be made of a transparent and colorless film. Here (as well as in the following), the term "film" includes a sheet.

The soundproof member 61 may also be made of a colored film that transmits colored laser beams. If the soundproof member 61 is made of a colored film, then the color of the film corresponds to the color of the laser beam to be used. For example, if the laser is red, then a red film is used; if green laser, a green film. If a colored film is used as the soundproof member 61 in such a way, then the laser beam used for marking is transmitted while the other colors of visible light are not. With the system in such a configuration, the subject P in position never sees the interior of the device through the soundproof member 61. Thus, the appearance of the system can be improved without imposing a strange feeling to the subject P.

The soundproof member 61 is made of a colored film alone. The soundproof member 61 may also be made of a combination of a colored film and a colorless, transparent film.

The colorless, transparent film is formed from a transparent and colorless resin. The colored film is formed by coloring the transparent and colorless resin.

For the coloration of the resin, coloring agents such as pigments and dyes are used. As pigments, inorganic and organic pigments are used. Dyes are selected and used, in consideration of mutual solubility with the resin. Dyes dissolve and spread in water, solvent, oil, etc. and show hues as results of absorbing particular visible rays. Dyes are suitable for coloration of transparent plastics because the molecules of dyes disperse.

Resin can be colored by the following two methods: 1) a coloring agent is melted and mixed and kneaded with the resin before forming; and 2) after the resin is formed, the formed article is colored with a coloring agent.

(Air Layer)

As mentioned previously, an air layer as soundproof layer 62 is sandwiched between two soundproof members 61. In this case, the air layer may be formed just by attaching the two soundproof members 61 to each other with pieces of double-stick tape 63 having a thickness of 0.5 mm-1.0 mm.

Providing an air layer can improve acoustic insulation. In addition, thickening the air layer lowers the frequency at which a coincidence effect takes place. FIG. 5 indicates with "f2" the frequency that has been decreased by the provision of the air layer. FIG. 5 also indicates with "t2" the upper limit of the thickness T of the soundproof member 61 for the frequency f2. As shown in FIG. 5, by increasing the upper limit of the thickness T of the soundproof member 61 to "t2", the thickness T of the soundproof member 61 can be increased (T<t2) to increase the value of acoustic transmission coefficient loss, thereby improving the acoustic insulation.

As shown in FIG. 6 and FIG. 7, the rear end 162d of the tubular opening front part 162a is provided with a recessed shelf 166, and the front end 163d of the tubular opening rear part 163a is also provided with a recessed shelf 166.

The relation between the depth of the recessed shelf 166 and the thickness of the double-stick tape 63 is expressed by the following expression (2)

$$D > 2T + t \quad (2)$$

where D indicates the depth of the recessed shelf 166, and t indicates the thickness of the double-stick tape 63.

Furthermore, the relations among the length of the double-stick tape 63, the width between both the recessed shelves 166, and the width of the X-ray transmission opening S1 in the Z-axis direction are expressed by the following expression (3)

$$W0 \geq W > W1 \quad (3)$$

where W indicates the length of the double-stick tape 63, W0 indicates the width between both the recessed shelves 166, and W1 indicates the width of the X-ray transmission opening Si in the Z-axis direction.

The stacking up of the two soundproof members 61 enhances the soundproof effect. In addition, the effect achieved with the thickness of the air layer improves the acoustic insulation (sound insulating properties) on in a range of low to middle tones.

The use of the double-stick tape 63 improves the sealability of the air layer, which, in turn, further improves the acoustic insulation.

The thickness of the air layer may be changed by modifying the thickness of the double-stick tape 63. By doing so, the predetermined frequency where a coincidence effect occurs can be lowered. In addition, these two soundproof members 61 may be disposed so as to define a predetermined angle between them. In this case, two double-stick tapes 63 having differing thicknesses may be applied, respectively, one on the rear end 162d of the tubular opening front part 162a and the other on the front end 163d of the tubular opening rear part 163a.

Described below is a procedure of closing the X-ray transmission opening S1 with the soundproof members 61.

At first, an adhesive is applied to the recessed shelves 166. Then, with the adhesive, one piece of soundproof member 61 is applied to stick onto the recessed shelves 166.

After that, a double-stick tape 63 is applied onto the piece of soundproof member 61 in position. Then, a second piece of soundproof member 61 is stuck on the double-stick tape 63.

By this procedure, the X-ray transmission opening S1 is closed with the soundproof members 61. In addition, by using the double-stick tape 63, the sticking of two pieces of soundproof member 61 is applied easily, and thus workability can be improved.

By the way, two pieces of soundproof member 61 that have been attached to each other with a double-stick tape 63 may be applied onto the recessed shelves 166. Instead, a double-stick tape 63 may be applied onto the recessed shelves 166 first, and then a first piece of soundproof member 61 may be applied onto the double-stick tape 63.

[Another Soundproof Construction]

Figure 8:
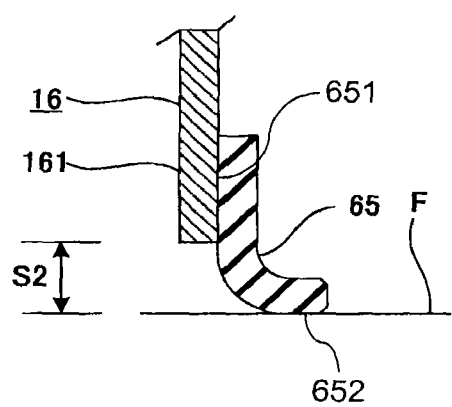
FIG. 8 is a sectional view of an elastic member, which is disposed to close the gap between the floor and the cover.

Now, an elastic member 65 is described with reference to FIG. 1, FIG. 3 and FIG. 8. FIG. 8 is a sectional view of the elastic member, which is disposed so as to close the gap S2 between the floor and the cover 16.

As shown in FIG. 1, FIG. 3, and FIG. 8, a gap S2 is provided between the room (floor F) where the X-ray CT system is installed and the lower edge of the bottom cover 161. The gap S2 is uneven. Since the unevenness is partly caused by imprecision involved in the production and assembly of the cover 16, it is not possible to install the system without a gap S2. With a gap S2, noises are leaked out from inside the cover 16. On the other hand, if the lower edge of the bottom cover 161 were in contact with the floor F, abnormal noises would be generated by vibration during the operation of the system.

The elastic member 65 is formed in a belt from an elastic material (e.g., plastic rubber). One edge 651 of the elastic member 65 is attached along the lower edge of the bottom cover 161. The other edge 652 of the elastic member 65 is in contact with the floor F, and this edge bends to the inside of the bottom cover 161. In this state, the resilience of the elastic member enables the elastic member to elastically touch the floor F. As a result, the gap S2 is banished.

By closing the gap S2 with the elastic member 65, the noise coming from inside the cover 16 can be reduced. Furthermore, since the edge of the elastic member 65 elastically touches the floor F, there is no abnormal noise which may be otherwise generated by vibration during the operation of the system.

The above-mentioned other edge 652 of the elastic member 65 is formed to bend to the inside of the bottom cover 161. As a result, the other edge 652 of the elastic member 65 in position hides itself in the bottom cover 161. This is an improvement to the appearance of the system.

Furthermore, the other edge 652 of the elastic member 65 is curved so as to bend to the inside of the bottom cover 161. Moreover, the thickness of the other edge 652 is made thinner than that of the other part including the one edge 651 so that the edge 652 can be easily bent.

In this embodiment, an acoustic absorption member may be attached to the internal surface of the cover 16. As an example of the acoustic absorption member, a porous material such as rock wool or glass wool is formed into a high-density plate to be used. It is preferable that a thin film of polyethylene or vinyl be used as an example of porous material.

In addition, in the embodiment, an acoustic reflection member, which has a property of reflecting and refracting incident sound entered into the internal surface of the cover 16.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of embodiments described herein may be made without departing from the spirit of the inventions. The accompanying claims and their equivalents are intended to cover such forms or modifications as would fall within the scope and spirit of the inventions.

DESCRIPTIONS OF NUMBERED PARTS

Letter P designates a subject;
S1, X-ray transmission opening;
S2, gap;
10, X-ray CT system;
11, gantry;
111, fan installation;
112, through-opening;
12, annular rotating body;
121, body axis;
122, air port;
13, frame;
15, opening;
16, cover;
161, bottom cover;
162, front cover;
162a, tubular opening front part;
163, rear cover;
163a, tubular opening rear part;
163b, vent;
164, ceiling cover;
164a, contact point;
165, lateral cover;
166, recessed shelf;
17, X-ray tube;
18, X-ray detector;
19, data acquisition part (DAS);
20, data transmitter;
21, console;
22, slip ring;
23, stationary part;
24, X-ray controller;
25, gantry controller;
26, radiator;
31, preprocessor;
32, bus line;
33, system controller;
34, input unit;
35, data storage;
36, reconstruction processor;
37, data processor;
38, display unit;
39, high voltage generator;
41, fan;
50, duct;
61, soundproof member;
62, soundproof layer;
63, double-stick tape;
65, elastic member;
70, bed; and
71, top plate.

What is claimed is:

1. An X-ray CT system, comprising:
an annular rotating body configured to accommodate an X-ray tube, the rotating body having an opening, into which a bed can be inserted in the center thereof;
a cover having a tubular case part shaped in a tubular form, which is fitted in the opening to shield the annular rotating body from a central side of the opening, the tubular case part being provided with an X-ray transmission opening through which X-rays from the X-ray tube are allowed to transmit; and
two sheet-like soundproof members configured to sandwich a soundproof layer, the soundproof members being disposed to close the X-ray transmission opening.

2. The X-ray CT system according to claim 1, wherein the soundproof members are formed from polyethylene terephthalate.

3. The X-ray CT system according to claim 1, wherein the soundproof layer is an air layer.

4. The X-ray CT system according to claim 1, wherein the thickness of the soundproof member is from 0.5 mm to 1.0 mm.

5. The X-ray CT system according to claim 4, wherein
a laser beam is irradiated onto a body surface of a subject that is mounted on the bed, for marking the body surface; and
the soundproof member comprises a colored film that allows the laser beam, which has a color, to transmit therethrough.

6. The X-ray CT system according to claim 5, wherein the soundproof member is formed by laminating the colored film with a colorless-transparent film.

7. The X-ray CT system according to claim 5, wherein the colored film is formed by kneading, into a colorless base material, a coloring agent that allows the colored laser beam to transmit therethrough.

8. The X-ray CT system according to claim 1, further comprising a double-stick tape, in which an adhesive is applied on both sides of thin film-like substrate, wherein
the two soundproof members are attached to each other with the double-stick tape.

9. The X-ray CT system according to claim 8, wherein the thickness of the double-stick tape is from 0.5 mm to 1.0 mm.

10. The X-ray CT system according to claim 1, wherein the soundproof layer is formed using an acoustic absorption sheet.

11. The X-ray CT system according to claim 10, wherein the acoustic absorption sheet is a porous material that includes glass wool.

12. The X-ray CT system according to claim 1, wherein the soundproof layer is formed using a sound reflector.

* * * * *